(12) United States Patent
Kito et al.

(10) Patent No.: US 7,465,320 B1
(45) Date of Patent: Dec. 16, 2008

(54) KNEE JOINT PROSTHESIS

(75) Inventors: Yukari Kito, Saitama (JP); Robert Metzger, Wakarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 797 days.

(21) Appl. No.: 10/840,765

(22) Filed: May 6, 2004

(51) Int. Cl.
  *A61F 2/38* (2006.01)
(52) U.S. Cl. .............. 623/20.27; 623/20.14; 623/20.21; 623/20.3; 623/20.31
(58) Field of Classification Search .............. 623/20.15, 623/20.19, 20.21, 20.24, 20.27, 20.28, 20.29
  See application file for complete search history.

(56) References Cited

U.S. PATENT DOCUMENTS

| | | | | |
|---|---|---|---|---|
| 4,938,769 A | * | 7/1990 | Shaw | 623/20.15 |
| 5,147,405 A | | 9/1992 | Van Zile et al. | |
| 5,330,532 A | | 7/1994 | Ranawat | |
| 5,330,534 A | | 7/1994 | Herrington et al. | |
| 6,165,223 A | * | 12/2000 | Metzger et al. | 623/20.27 |
| 6,168,629 B1 | * | 1/2001 | Timoteo | 623/20.27 |
| 6,203,576 B1 | | 3/2001 | Afriat et al. | |
| 6,264,697 B1 | * | 7/2001 | Walker | 623/20.27 |
| 6,325,828 B1 | * | 12/2001 | Dennis et al. | 623/20.14 |
| 6,443,991 B1 | | 9/2002 | Running | |
| 7,081,137 B1 | * | 7/2006 | Servidio | 623/20.14 |
| 2003/0004577 A1 | * | 1/2003 | Running | 623/20.27 |
| 2004/0186582 A1 | * | 9/2004 | Yasuda et al. | 623/20.21 |
| 2004/0243244 A1 | * | 12/2004 | Otto et al. | 623/20.27 |
| 2005/0143832 A1 | * | 6/2005 | Carson | 623/20.28 |
| 2007/0135925 A1 | * | 6/2007 | Walker | 623/20.21 |
| 2007/0135926 A1 | * | 6/2007 | Walker | 623/20.31 |

* cited by examiner

*Primary Examiner*—Thomas J Sweet
*Assistant Examiner*—Jonathan R Stroud
(74) *Attorney, Agent, or Firm*—Harness, Dickey & Pierce, P.L.C.

(57) ABSTRACT

A knee joint prosthesis including a femoral component for attachment to a femur. The femoral component includes an anterior portion, first and second condylar portions extending from the anterior portion and having first and second bearing surfaces, the first and second condylar portions having first and second posterior ends, and a third condylar portion defined between the first and second condylar portions and extending anteriorly beyond the first and second posterior ends.

21 Claims, 8 Drawing Sheets

KNEE JOINT PROSTHESIS

Early total knee prostheses were designed to meet the demands of daily living of older, relatively sedate patients in the West. Today, however, younger and more active patients around the world, including athletes, are candidates for knee joint implants. These patients expect to pursue post-surgery their active lifestyle, and/or daily socio-cultural and religious activities, which may require frequent deep flexion, including kneeling and squatting. Additionally, certain work-related activities involve repeated motions that require deep flexion, such as, for example, sitting/standing up, lifting an object, ascending/descending stairs. All these activities demand an extensive range of motion for the knee joint. Kneeling and full squatting, for example, are estimated to require an angle of flexion in the range of 110°-165°, although such estimates vary with the individual. Furthermore, because this greater range of motion is repeated many times daily, wear and fatigue resistance of the components of the knee joint prosthesis are critical.

There is, therefore, a need for improved knee joint prosthesis that affords a greater range of motion and wear/fatigue resistance.

SUMMARY

The present teachings provide a knee joint prosthesis that includes a femoral component for attachment to a femur. The femoral component includes an anterior portion, first and second condylar portions extending from the anterior portion and having first and second bearing surfaces, the first and second condylar portions having first and second posterior ends, and a third condylar portion defined between the first and second condylar portions and extending anteriorly beyond the first and second posterior ends. In one aspect the third condylar portion extends anteriorly beyond a posterior resection plane of the femur.

The present teachings provide a knee joint prosthesis that includes a tibial component for attachment to a tibia and a femoral component for attachment to a femur. The tibial component includes a tibial bearing and a tibial base. The femoral component includes lateral, medial and central condylar portions. The lateral and medial condylar portions articulate with respective lateral and medial bearing surfaces of the tibial bearing. The central condylar portion extends anteriorly beyond respective posterior ends of the lateral and medial condylar portions. In another aspect, the central condylar portion articulates with and maintains an area contact with a portion of the tibial bearing in deep flexion.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description is merely exemplary in nature and is in no way intended to limit the invention, its application, or uses. In this regard, while the invention is described in detail below generally with respect to exemplary knee joint prostheses, the invention is not limited to those prostheses, but can be applied to other types of knee joint prostheses, including posterior stabilized (PS), cruciate retaining (CR), fully constrained, or hinged prostheses, and to prostheses with fixed, mobile or floating tibial bearings, etc.

Figure 1:
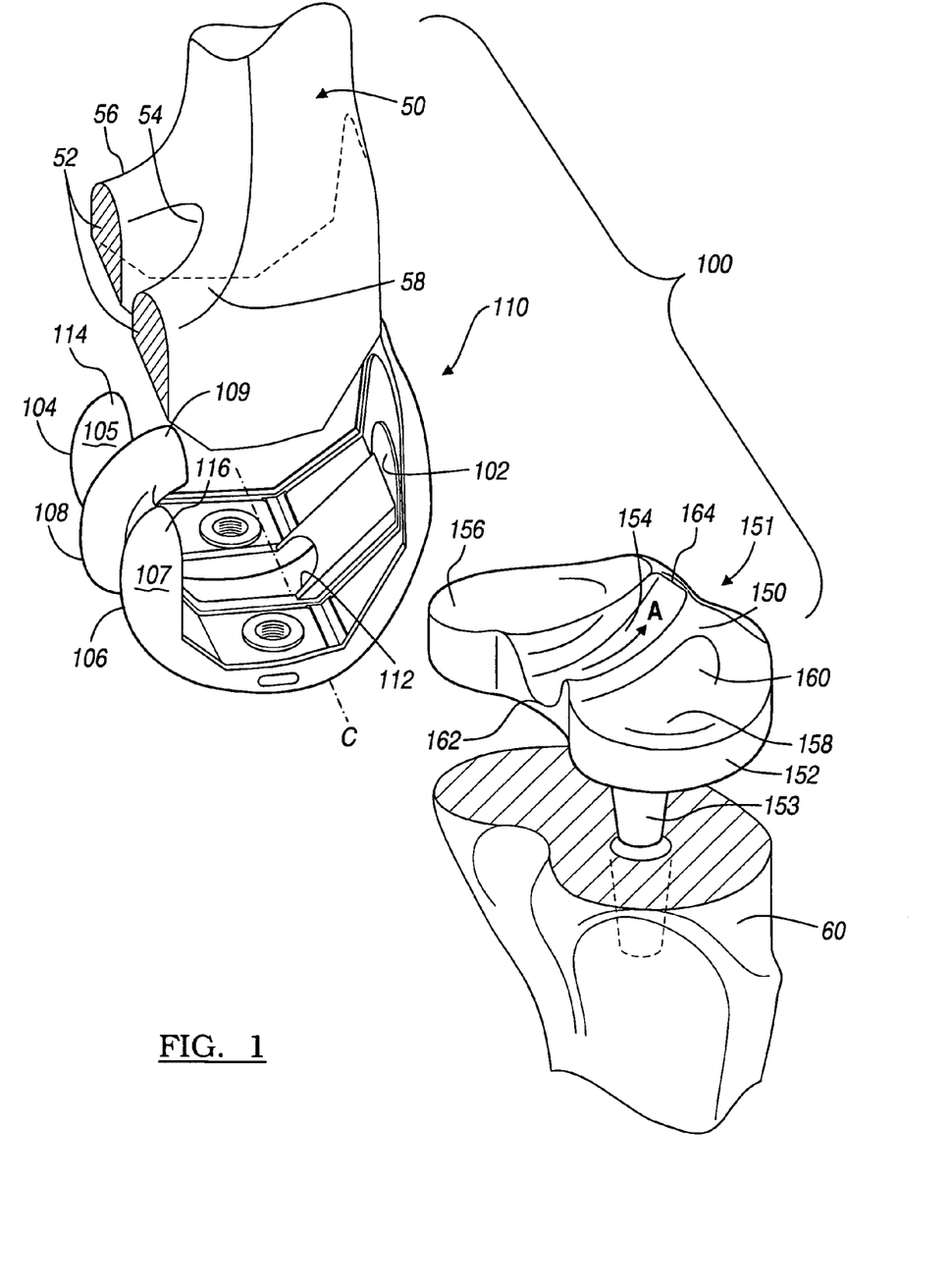
FIG. 1 is an environmental exploded perspective view of a knee joint prosthesis according to the present teachings, shown at 0° of flexion.

Referring to FIG. 1, an exemplary posterior stabilized (PS) knee joint prosthesis 100 according to the present teachings includes a femoral component 110 for attachment to a resected femur 50, and tibial component 151. The tibial component 151 can include a tibial bearing 150 for articulation with the femoral component 110, and a tibial base 152 coupling the tibial bearing 150 with the tibia 60. The lateral and medial condyles of the femur 50 are resected posteriorly along a posterior resection plane 52, and the tibia 60 is also resected to define a tibial plateau for receiving the tibial base 152. The shape, articulation and engagement of the femoral component 110, the tibial bearing 150, and the tibial base 152 can be of any type known in the art, such as described, for example, in co-owned U.S. Pat. No. 6,589,283, No. 6,413,279, and No. 6,165,223, all of which are incorporated herein by reference. Additionally, the tibial bearing 150 can be integrally or modularly coupled to the tibial base 152.

Figure 1A:
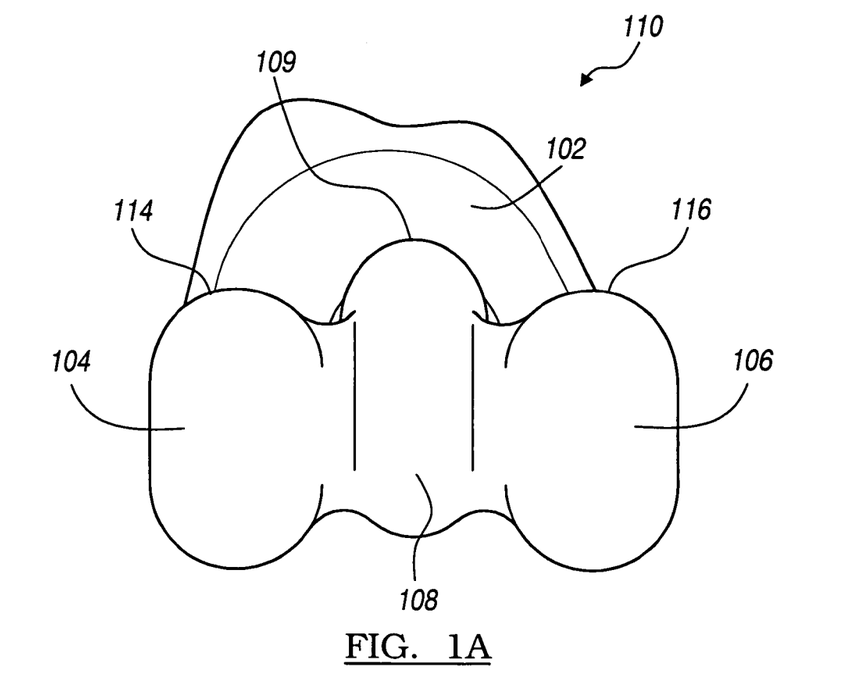
FIG. 1A is a posterior view of the femoral component of FIG. 1.
Figure 1B:
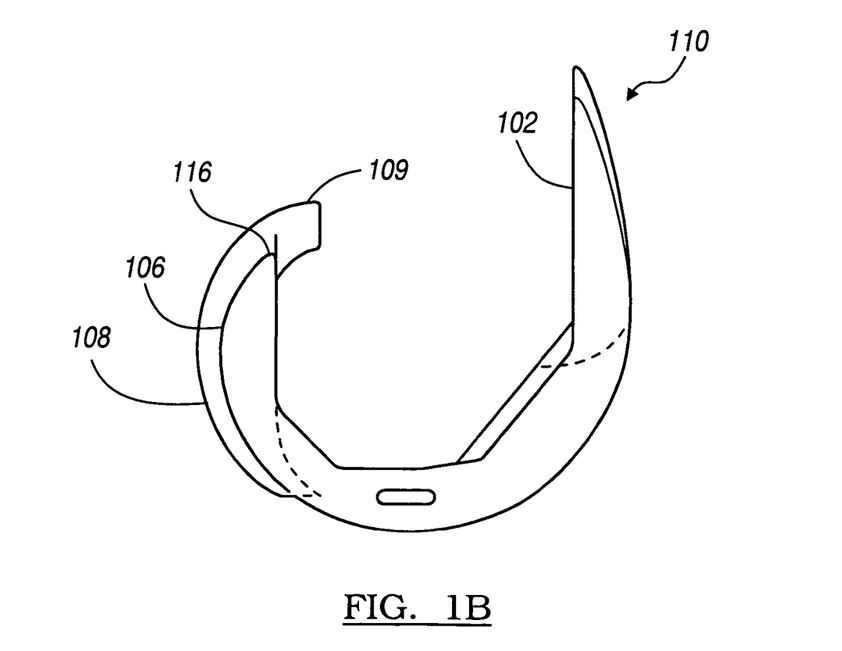
FIG. 1B is a side view of the femoral component of FIG. 1.
Figure 2:
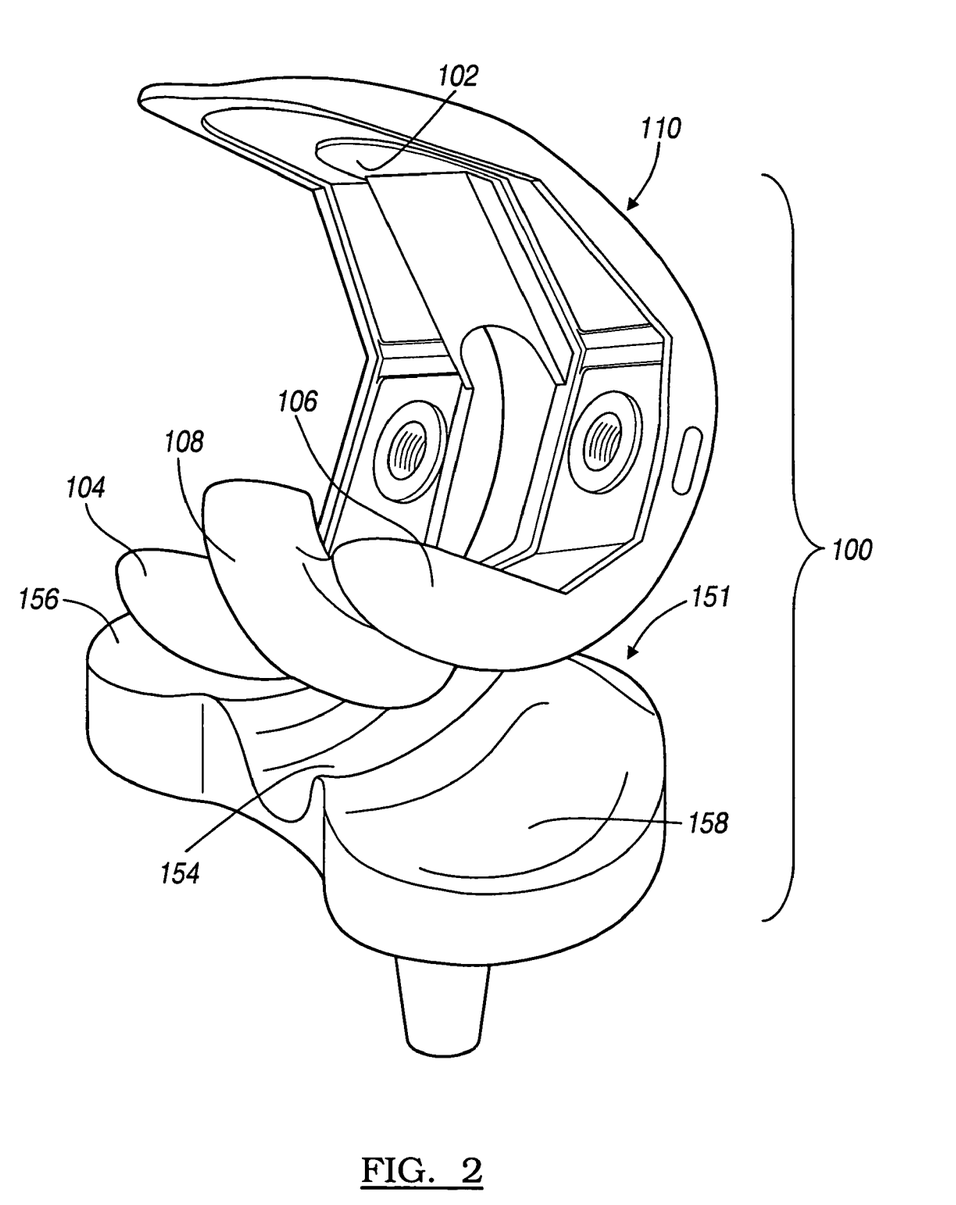
FIG. 2 is a perspective view of the knee joint prosthesis of FIG. 1, shown at 90° of flexion.

The femoral component 110 has an anterior portion 102 and lateral and medial condylar portions 104, 106 extending from the anterior portion 102 posteriorly and corresponding to the respective natural femoral condyles, as is generally known in the art. The lateral and medial condylar portions 104, 106 include respective bearing surfaces 105, 107 for articulation with the tibial bearing 150. The lateral and medial condylar portions 104, 106 have respective lateral and medial posterior ends 114, 116. The femoral component 110 also includes a central condylar portion (or central cam) 108 defined between the lateral and medial condylar portions 104, 106. The central condylar portion 108 extends anteriorly and superiorly beyond the posterior ends 114, 116 by an extension 109. The central condylar portion 108 extends into the opening of the intercondylar notch 54 defined by the natural lateral and medial femoral condyles 56, 58, which are resected along the posterior resection plane 52. As such, the extended central condylar portion 108 is bone-preserving and does not require additional resection of the femur 50. In one aspect, the femoral component 110 may include an intercondylar opening 112.

The extension 109 of the central condylar portion 108 extends anteriorly and superiorly relative to the posterior resection plane 52 of the femur 50. The central condylar portion 108 is has a radius of curvature that can be concentric with the radii of curvature of the lateral and medial condylar portions 104, 106, such that all three condylar portions 104, 106, 108 rotate in flexion about a common axis C. It will be appreciated however, that the central condylar portion 108 and the lateral and medial condylar portions 104, 106 can have different axes of curvature while incorporating respective curvature adjustments in the tibial bearing 150. Furthermore, although the lateral and medial condylar portions 104, 106 are illustrated as singly curved, doubly curved lateral and medial condylar portions 104, 106 are also within the scope of the invention.

The tibial bearing 150 can be modularly or integral coupled with the base 152 for attachment to a resected tibia 60. Thus the tibial bearing 150 can be of the fixed, mobile or floating type. The base 152 can include an anchor 153 modularly or integrally coupled to the base 152 for attachment to the tibia 60. The anchor 153 can be, for example, a peg, a post, a keel, and can include porous coating, threading and attachment fins. The tibial bearing 150 has a proximal surface 160 that includes lateral and medial articulating portions 156, 158, singly or doubly curved, for articulation with the bearing surfaces 105, 107 of the lateral and medial condylar portions 104, 106 of the femoral component 110. The proximal surface 160 defines a groove 154 between the lateral and medial articulating portions 156, 158. The groove 154 has posterior and anterior ends 162, 164 and rises gradually in the anterior direction indicated by arrow "A".

Figure 3:
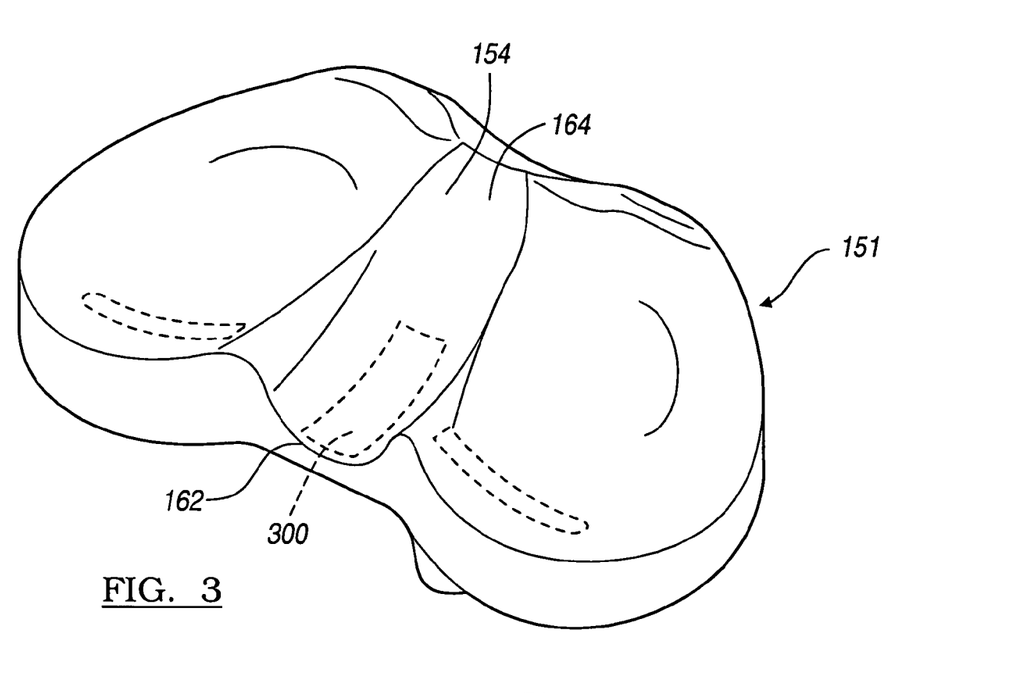
FIG. 3 is a top perspective view of the tibial component of FIG. 1 illustrating the contact area between the central condylar portion and the tibial component at 90° of flexion.
Figure 4:
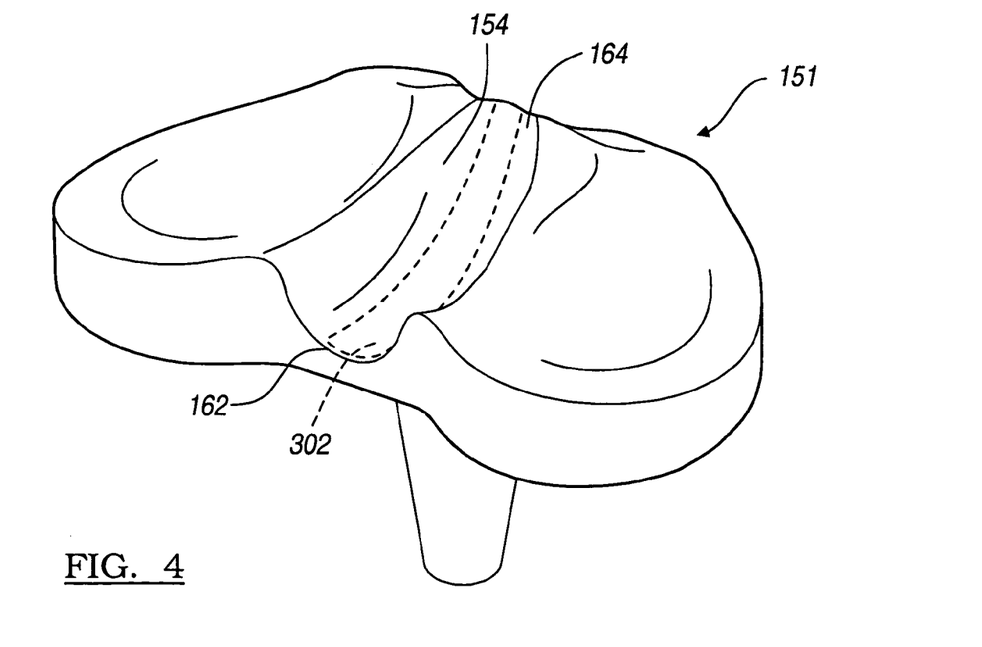
FIG. 4 is a top perspective view of the tibial component of FIG. 1 illustrating the contact area between the central condylar portion and the tibial component at 135° of flexion.

Referring to FIGS. 1-4, the tibial groove 154 and the central condylar portion 108 of the femoral component 110 are sized and shaped for articulation during flexion, such that area contact, and not merely line contact, can develop therebetween extending over a contact area 300. The contact area 300 starts at the posterior end 162 of the groove at an angle of flexion of about 45° as a line contact and continuously spreads to the anterior end 164 as the angle of flexion increases. Full contact, defined as contact over a contact area 302 that extends over the entire length of the groove 154 from the posterior end 162 to the anterior end 164 is established at about 120° angle of flexion. The actual coverage of the full contact area depends on the particular knee prosthesis and is typically about 200 to 400 mm². Full contact is maintained up to an angle of flexion about 150°-160°. FIG. 3 illustrates the contact area 300 for an angle of flexion of 90°. FIG. 4 illustrates the full contact area 302 for an angle of flexion 135°. For an angle of flexion greater than about 150°-160°, a portion of the full contact area 302 is gradually lost from the posterior end 162, but area contact is still maintained for angles of flexion greater than 160°. Furthermore, contact between the bearing surfaces 105, 107 of the lateral and medial condylar portions 104, 106 with the lateral and medial articulating portion 156, 158 of the tibial bearing 150 is maintained during flexion. The type of contact, i.e. line or area contact, and the extent of contact area, if any, depends on the particular configuration of the respective bearing surfaces of the femoral component 110 and the tibial bearing 150, and it can be accordingly adjusted. For example, a contact area of greater than about 300 mm² between the bearing surfaces 105, 107 of the lateral and medial condylar portions 104, 106 with the lateral and medial articulating portion 156, 158 of the tibial bearing 150 is maintained from extension to full flexion for the knee prosthesis of U.S. Pat. No. 6,413,279.

It will be appreciated from the foregoing that the extended length of the central condylar portion 108 enables area contact, and not just line contact, for flexion at angles greater than 45°, including deep flexion. Considering that the angle of flexion for various normal activities seldom, if ever, reaches angles greater than 160°, area contact develops and the contact area 300 increases for the practical limits of deep flexion. Ascending and descending stairs, for example, has been estimated to have a functional range of 0°-90°, depending on the height of the individual and the height of the steps. Squatting and kneeling can reach up to about 165°. Although the theoretical limit of deep flexion is 180°, the thickness of the femur and tibia and associated soft tissues generally preclude such angle. The extensive area contact that is permitted during deep flexion by the knee joint prosthesis 100, results in better load distribution, reduces contact pressure, reduces wear and associated debris, increases stability and extends the life of the prosthesis, while affording the patient a practically unlimited range of motion without sacrificing additional femoral bone. Additionally, high loads caused by edge contact of the lateral and medial condylar portions 104, 106 with the lateral and medial articulating portions 156, 158 of the tibial bearing 150, and associated wear, are avoided by providing additional contact between the central condylar portion 108 and tibial groove 154 in deep flexion, for angles greater than 150°, for example. Patients of smaller stature engaging in strenuous activities requiring deep flexion, and patients whose daily cultural and social activities require frequent kneeling and squatting are particularly benefited by the extended deep flexion capabilities of the knee joint prosthesis 100.

Figure 5:
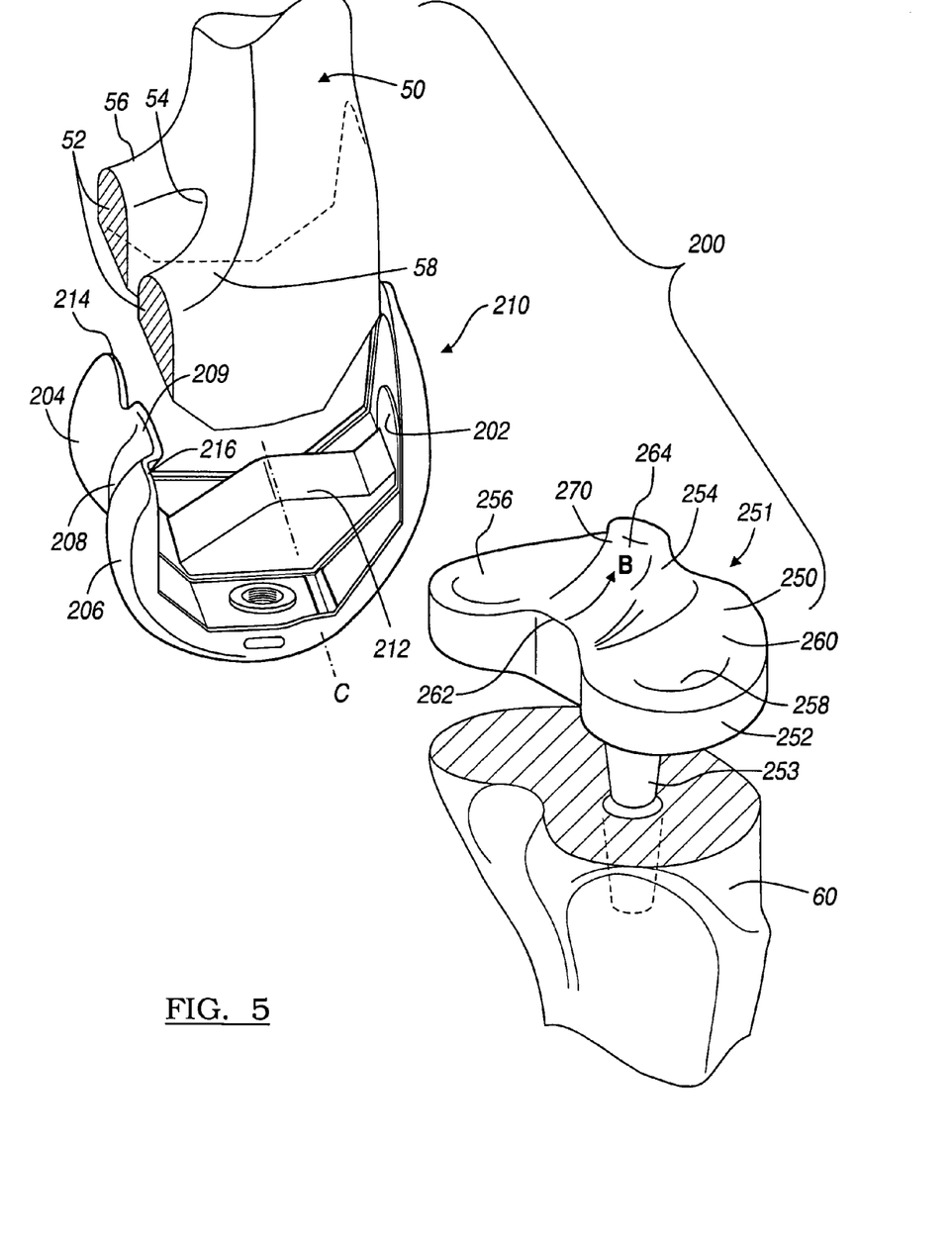
FIG. 5 is an environmental exploded perspective view of a knee joint prosthesis according to the present teachings, shown at 0° of flexion.

Referring to FIG. 5, an exemplary posterior-stabilized (PS) knee joint prosthesis 200 according to the present teachings includes a femoral component 210 for attachment to the resected femur 50, and a tibial component 251. The tibial component 251 can include a tibial bearing 250 for articulation with the femoral component 210. The femoral component 210 has an anterior portion 202 and lateral and medial condylar portions 204, 206 extending from the anterior portion 202 posteriorly. The lateral and medial condylar portions 204, 206 have respective lateral and medial posterior ends 214, 216. The femoral component 210 also includes a central condylar portion (or central cam) 208 defined between the lateral and medial condylar portions 204, 206. The central condylar portion 208 extends anteriorly beyond the posterior ends 214, 216 by an extension 209. The central condylar portion 208 extends into the opening of the intercondylar notch 54 defined by the natural lateral and medial femoral condyles 56, 58, which are resected along the posterior resection plane 52. As such, the extension 209 of the central condylar portion 208 is bone-preserving and does not require additional resection of the femur 50.

Figure 5A:
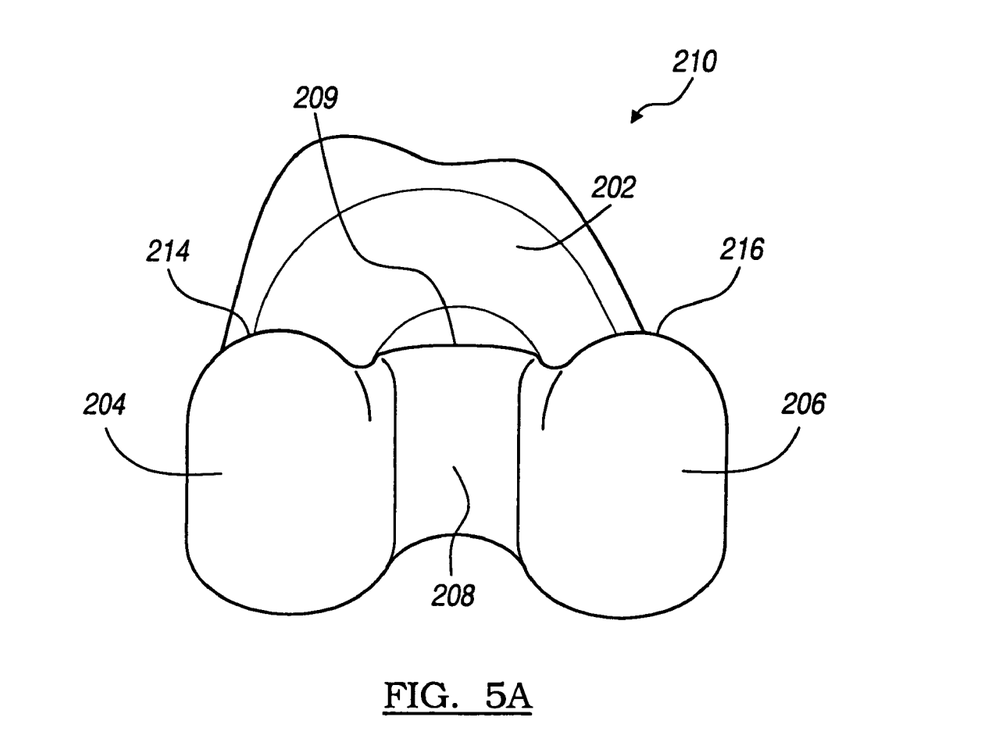
FIG. 5A is a posterior view of the femoral component of FIG. 5.
Figure 5B:
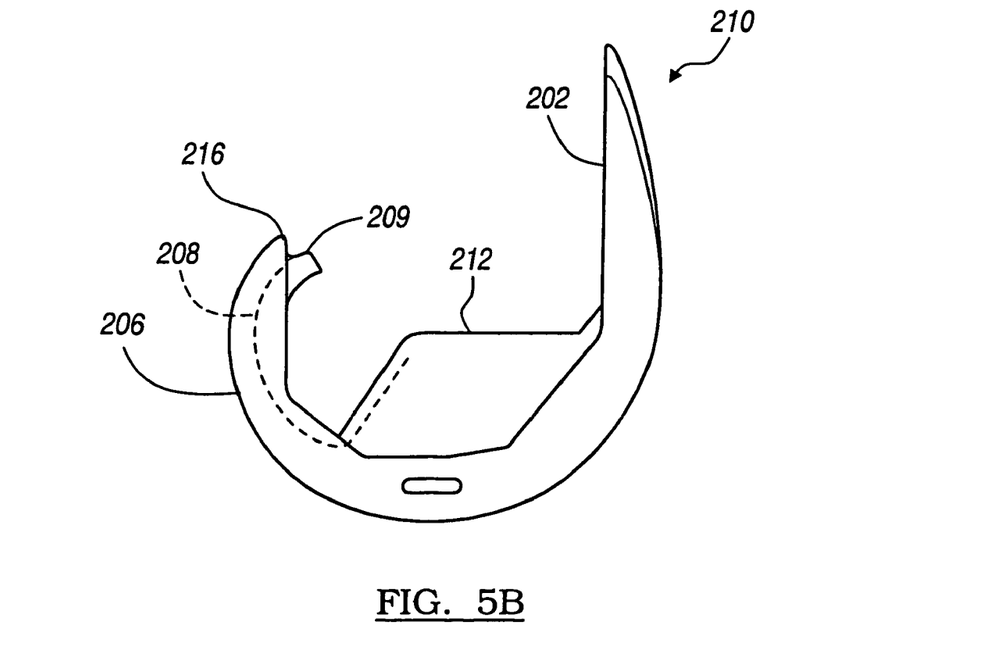
FIG. 5B is a side view of the femoral component of FIG. 5.
Figure 6:
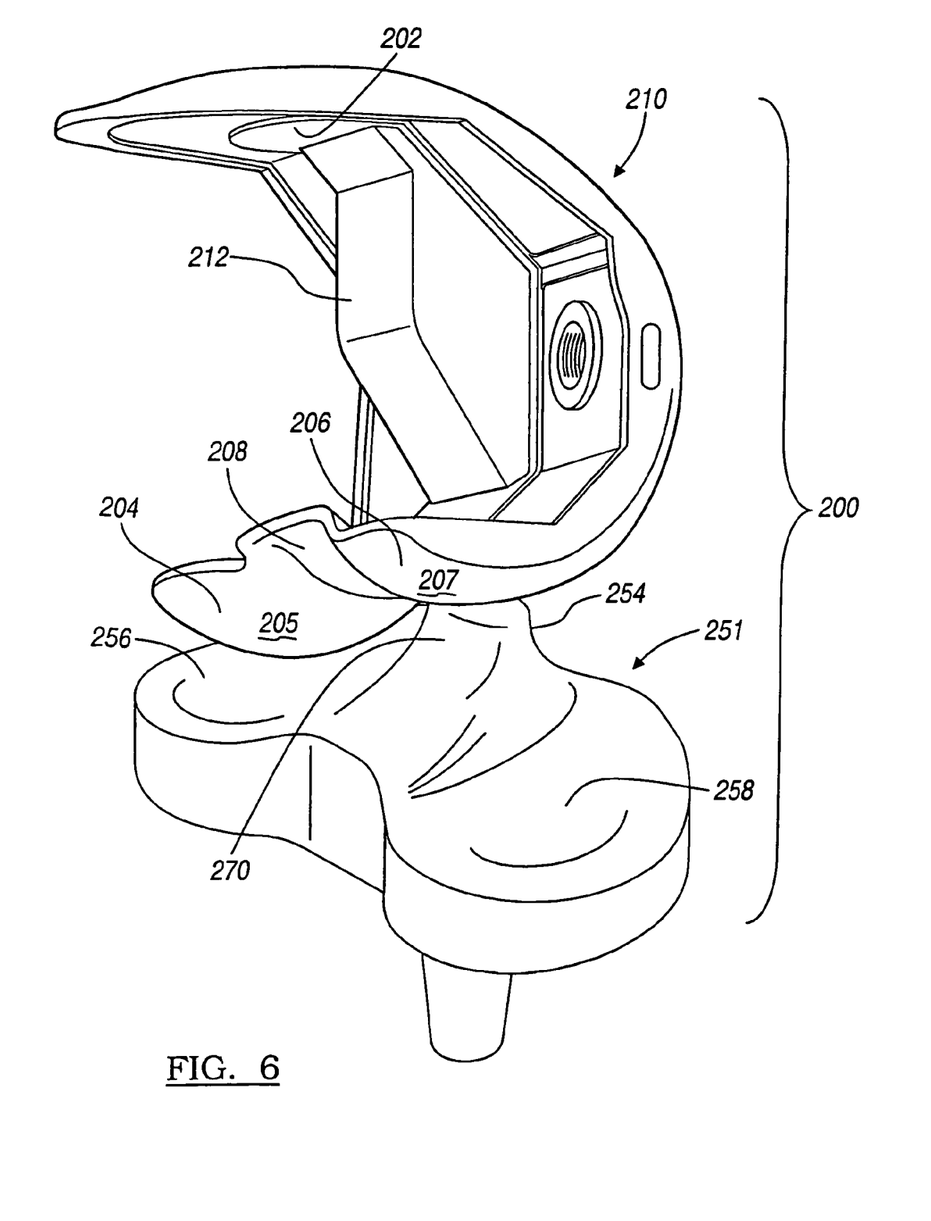
FIG. 6 is a perspective view of the knee joint prosthesis of FIG. 5, shown at 90° of flexion.

In particular, the extension 209 of the central condylar portion 208 extends anteriorly relative to the posterior resection plane 52 of the femur 50. The central condylar portion 208 is has a radius of curvature that is concentric with the radii of curvature of the lateral and medial condylar portions 204, 206, such that all three condylar portions 204, 206, 208 rotate in flexion about a common axis C. It will be appreciated however, that the central condylar portion 208 and the lateral and medial condylar portions 204, 206 can have different axes of curvature while incorporating respective curvature adjustments in the tibial bearing 150. In one aspect, the femoral component 210 can include an intercondylar box 212 which can be of the open or closed type, although a closed intercondylar box 212 is illustrated in FIG. 5.

The tibial bearing 250 can be modularly or integrally coupled with the base 252 for attachment to a resected tibia 60. Thus the tibial bearing 250 can be of the fixed, mobile or floating type. The base 252 can include an anchor 253 modularly or integrally coupled to the base 252 for attachment to the tibia 60. The anchor 253 can be, for example, a peg, a post, a keel, and can include porous coating, threading and attachment fins. The tibial bearing 250 has a proximal surface 260 that includes lateral and medial articulating portions 256, 258 for articulation with the lateral and medial condylar portions 204, 206 of the femoral component 110. The proximal surface 260 defines a post or spine 254 between the lateral and medial articulating portions 256, 258. The post 254 has posterior and anterior ends 262, 264 along an articulating surface 270, which rises gradually in the anterior direction indicated by arrow "B".

Figure 7:
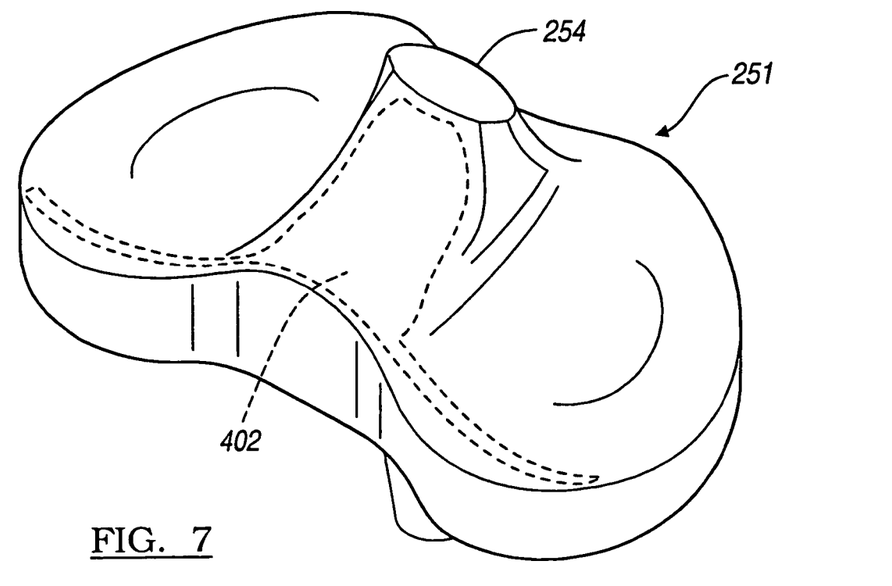
FIG. 7 is a top perspective view of the tibial component of FIG. 5 illustrating the contact area between the central condylar portion and the tibial component at 90° of flexion.
Figure 8:
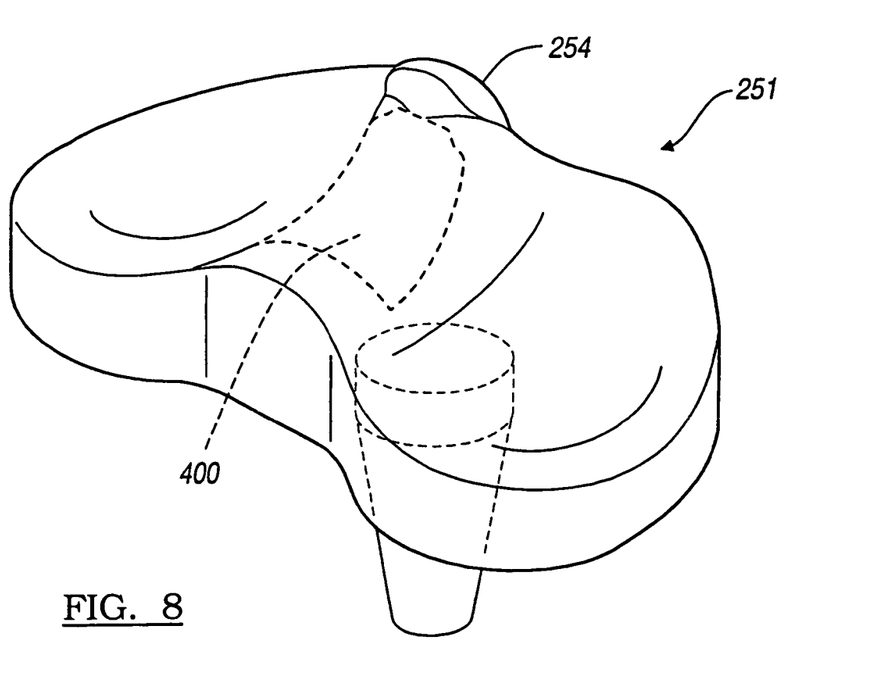
FIG. 8 is a top perspective view of the tibial component of FIG. 5 illustrating the contact area between the central condylar portion and the tibial component at 150° of flexion.

Referring to FIGS. 5-8, the tibial post 254 and the central condylar portion 208 of the femoral component 210 are sized and shaped for articulation during flexion, such that area contact, and not merely line contact, can develop therebetween extending over a contact area 402. The contact area 402 is a full contact area that extends over the entire length of the post 254 from the posterior end 262 to the anterior end 264 and is established at about 15°-20° of flexion. Full contact is maintained up to an angle of flexion about 130°-140°. The actual coverage of the full contact area depends on the particular knee prosthesis and is typically about 200 to 600 mm². FIG. 7 illustrates the full contact area 402 for an angle of flexion of 900. For an angle of flexion greater than about 130°-140°, a portion of the full contact area 402 is gradually lost from the posterior end 262, but area contact is still maintained for angles of flexion greater than 140°. FIG. 8 illustrates a contact area 400 for an angle of flexion 150°.

The benefits of the extensive area contact that result from the extended central condylar portion 108 of the knee joint prosthesis 100, are also available for the posterior-stabilized knee joint prosthesis 200, which also includes an extended central condylar portion 208. The posterior-stabilized knee joint prosthesis 200 provides a full contact area 402 between the central condylar portion 208 and the articulating surface 270 of the post 254 over a wide range of angles of flexion, as discussed above. Therefore, high loads caused by edge contact of the lateral and medial condylar portions 204, 206 with the lateral and medial articulating portions 256, 258 of the tibial bearing 250, and associated wear, are avoided by providing additional contact between the central condylar portion 208 and the articulating surface 270 of the post 254 in deep flexion, for angles greater than 150°, for example. Therefore, the knee joint prosthesis 200 results in better load distribution, reduces contact pressure, reduces wear and associated debris, increases stability and extends the life of the prosthesis, without sacrificing additional femoral bone.

The femoral component 110, 210 and the tibial base 152, 252 can be each made as a unitary structure from a biocompatible high strength alloy, such as cobalt-chromium-molybdenum alloy, or other biocompaticle material. The tibial bearing 150, 250, the anchor 153, 253, and the tibial post 254 can be made from a surgical grade, low friction, wear-resistant plastic, such as ultra-high molecular weight polyethylene (UHMWPE), or other biocompatible materials including metal, ceramic, polymer, etc., or combinations thereof. The tibial bearing 250 can be integrally or modularly coupled to tibial base 252 and/or the tibial post 254, and the tibial bearing 150 can be integrally or modularly coupled to tibial base 252.

While particular embodiments have been described in the specification and illustrated in the drawings, it will be understood by those skilled in the art that various changes may be made and equivalents may be substituted for elements thereof without departing from the scope of the invention as defined in the claims. In addition, many modifications may be made to adapt a particular situation or material to the present teachings without departing from the essential scope thereof. Therefore, it is intended that the present teachings are not be limited to the particular embodiments illustrated by the drawings and described in the specification, but that the present teachings will include any embodiments falling within the foregoing description and the appended claims.

What is claimed is:

1. A knee joint prosthesis comprising:
   a tibial component for attachment to a tibia, the tibial component having a medial bearing surface, a lateral bearing surface and a central bearing surface between the medial and lateral bearing surfaces;
   a femoral component for attachment to a femur, the femoral component comprising:
   an anterior portion;
   medial and lateral condylar portions extending from the anterior portion along a posterior condylar length to respective medial and lateral posterior ends of the medial and lateral condylar portions, the medial and lateral condylar portions having first and second medial and lateral bearing surfaces configured for articulation with the medial and lateral bearing surfaces of the tibial component; and
   a central condylar portion defined between the medial and lateral condylar portions and extending and attached to the medial and lateral condylar portions along substantially the entire posterior condylar length, being unitarily attached with the lateral and medial condylar portions forming one piece, the central condylar portion having an a superior extension extending anteriorly beyond the medial and lateral posterior ends, the superior extension extending in a superior direction relative to the medial and lateral posterior ends beyond a resection plane of the femur and articulating and maintaining area contact with the central bearing surface of the tibial component in deep flexion, the central condylar portion having a radius of curvature that is substantially concentric with the radii of curvature of the lateral and medial condylar portions.

2. The knee joint prosthesis of claim 1, wherein the medial and lateral condylar portions articulate with and maintains area contact with the medial and lateral bearing surfaces of the tibial component in deep flexion.

3. The knee joint prosthesis of claim 2, wherein deep flexion includes flexion of at least 150°.

4. The knee joint prosthesis of claim 1, wherein area contact with full contact is established between the central condylar portion and the central bearing surface of the tibial component at angles of flexion in the range of about 15°-20°.

5. The knee joint prosthesis of claim 4, wherein area contact gradually decreases posteriorly from full contact for angles of flexion greater than about 130°-140°.

6. The knee joint prosthesis of claim 1, wherein the medial, lateral and central condylar portions have articular surfaces with equal radii of curvature and coincident axes of curvature.

7. The knee joint prosthesis of claim 1, wherein the tibial component includes a tibial bearing and a tibial base coupled to the tibial bearing.

8. The knee joint prosthesis of claim 7, wherein the tibial bearing is modularly coupled to the tibial base.

9. A knee joint prosthesis comprising:

a tibial component;

a femoral component for attachment to a femur, the femoral component comprising:

an anterior portion;

lateral and medial condylar portions extending from the anterior portion along a posterior condylar length to respective first and second lateral and medial posterior ends; and a central condylar portion defined between the lateral and medial condylar portions and attached to the lateral and medial condylar portions along substantially the entire posterior condylar length in a posterior-anterior direction, being unitarily attached with the lateral and medial condylar portions forming one piece, the central condylar portion having a superior extension oriented in the posterior-anterior direction, the extension extending anteriorly beyond a posterior resection plane of the femur, the superior extension extending in a superior direction relative to the lateral and medial posterior ends to maintain area contact with a bearing surface of the tibial component during deep flexion the central condylar portion having a radius of curvature that is substantially concentric with the radii of curvature of the lateral and medial condylar portions.

10. A knee joint prosthesis comprising:

a tibial component for attachment to a tibia, the tibial component comprising:

a tibial base; and a tibial bearing coupled to the tibial base and having lateral and medial bearing surfaces and a central bearing surface between the lateral and medial bearing surfaces; and a femoral component for attachment to a femur, the femoral component comprising:

an anterior portion; lateral and medial condylar portions extending from the anterior portion for articulating with the lateral and medial bearing surfaces of the tibial bearing, the lateral and medial condylar portions extending along a posterior condylar length to respective lateral and medial posterior ends; and a central condylar portion attached to the lateral and medial condylar portions along substantially the entire posterior condylar length, being unitarily attached with the lateral and medial condylar portions forming one piece, the central condylar portion having an a superior extension extending anteriorly beyond the respective lateral and medial posterior ends of the lateral and medial condylar portions and beyond a posterior resection plane of the femur, the superior extension extending in a superior direction relative to the lateral and medial posterior ends, the superior extension articulating and maintaining area contact with the central bearing surface of the tibial component in deep flexion, the central condylar portion having a radius of curvature that is substantially concentric with the radii of curvature of the lateral and medial condylar portions.

11. The knee joint prosthesis of claim 10, wherein flexion includes flexion of at least 150°.

12. The knee joint prosthesis of claim 10, wherein the femoral component includes an intercondylar opening extending between the anterior portion and the central condylar portion.

13. The knee joint prosthesis of claim 10, wherein area contact occurs for angles of flexion greater than about 45°.

14. The knee joint prosthesis of claim 10, wherein the central bearing surface of the tibial bearing articulating with the central condylar portion is an articulating surface of a tibial post.

15. The knee joint prosthesis of claim 14, wherein the femoral component includes an intercondylar box between the anterior portion and the central condylar portion.

16. The knee joint prosthesis of claim 14, wherein area contact occurs for angles of flexion greater than about 15°-20°.

17. The knee joint prosthesis of claim 10, wherein the tibial bearing is integral to the tibial base.

18. The knee joint of claim 10, wherein the tibial bearing is of a type selected from the group consisting of fixed, mobile, and floating.

19. The knee joint prosthesis of claim 10, wherein the tibial base includes an anchor selected from the group consisting of peg, post, and keel.

20. The knee joint prosthesis of claim 19, wherein the anchor is modularly connected to the tibial base.

21. The knee prosthesis of claim 14, wherein the tibial post is modularly connected to the tibial component.

* * * * *

UNITED STATES PATENT AND TRADEMARK OFFICE
CERTIFICATE OF CORRECTION

| | |
|---|---|
| PATENT NO. | : 7,465,320 B1 |
| APPLICATION NO. | : 10/840765 |
| DATED | : December 16, 2008 |
| INVENTOR(S) | : Kito et al. |

It is certified that error appears in the above-identified patent and that said Letters Patent is hereby corrected as shown below:

Column 3
Line 21, "integral" should be --integrally--.

Column 6
Line 27, delete "first and second".
Line 37, delete "an".

Column 7
Line 8, delete "first and second".
Line 36, insert paragraph break after "portion;".

Column 8
Line 34, insert --prosthesis-- after "joint".

Signed and Sealed this

Third Day of March, 2009

JOHN DOLL
*Acting Director of the United States Patent and Trademark Office*